(12) United States Patent
Smith et al.

(10) Patent No.: US 12,702,419 B2
(45) Date of Patent: Aug. 11, 2026

(54) ENDOCARDIAL LEFT ATRIAL APPENDAGE MANAGEMENT

(71) Applicant: Wake Forest University Health Sciences, Winston-Salem, NC (US)

(72) Inventors: James A. Smith, Winston-Salem, NC (US); James E. Johnson, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 305 days.

(21) Appl. No.: 17/919,805

(22) PCT Filed: Apr. 23, 2021

(86) PCT No.: PCT/US2021/028784
§ 371 (c)(1),
(2) Date: Oct. 19, 2022

(87) PCT Pub. No.: WO2021/216962
PCT Pub. Date: Oct. 28, 2021

(65) Prior Publication Data

US 2023/0074249 A1 Mar. 9, 2023

Related U.S. Application Data

(60) Provisional application No. 63/014,363, filed on Apr. 23, 2020.

(51) Int. Cl.
*A61B 17/12* (2006.01)
*A61B 18/14* (2006.01)
(Continued)

(52) U.S. Cl.
CPC .... *A61B 17/12013* (2013.01); *A61B 18/1492* (2013.01); *A61B 2017/00349* (2013.01);
(Continued)

(58) Field of Classification Search
CPC .............. A61B 17/12; A61B 17/12122; A61B 17/12013; A61B 17/12027;
(Continued)

(56) References Cited

U.S. PATENT DOCUMENTS 5,417,697 A * 5/1995 Wilk ...................... A61B 18/10 606/115
6,039,729 A * 3/2000 Durville ............ A61B 18/1445 606/16
(Continued)

OTHER PUBLICATIONS

ISR and Written Opinion for PCT Application No. PCT/US2021/028784 mailed Aug. 18, 2021.
(Continued)

*Primary Examiner* — Tuan V Nguyen
(74) *Attorney, Agent, or Firm* — Kilpatrick Townsend & Stockton LLP

(57) ABSTRACT

Disclosed are methods and devices for endocardial left atrial appendage management (LAAM) by inversion and excision. The methods may comprise inserting an inverter apparatus into an interior cavity of the left atrial appendage (LAA) of a subject and inverting the LAA, closing the base portion of the inverted LAA with the one or more closure devices, separating the inverted LAA from the left atrium with a separation apparatus positioned at the base portion of the inverted LAA adjacent to the one or more closure devices, and removing the separated LAA from the subject.

15 Claims, 16 Drawing Sheets

(51) Int. Cl.
*A61B 17/00* (2006.01)
*A61B 18/00* (2006.01)

(52) U.S. Cl.
CPC ............... *A61B 2017/00871* (2013.01); *A61B 2018/00357* (2013.01); *A61B 2018/00595* (2013.01)

(58) Field of Classification Search
CPC .... A61B 17/12031; A61B 2017/00349; A61B 2017/00871; A61B 18/1492
See application file for complete search history.

(56) References Cited

U.S. PATENT DOCUMENTS 7,828,810 B2 11/2010 Liddicoat et al.
8,932,308 B2 1/2015 Ibrahim et al.
2002/0111636 A1 8/2002 Fleischman et al.
2008/0015569 A1* 1/2008 Saadat ............... A61B 5/02007 606/41
2008/0125795 A1* 5/2008 Kaplan .............. A61B 17/1285 606/140
2008/0294175 A1* 11/2008 Bardsley ............ A61B 17/1285 606/113
2011/0077672 A1* 3/2011 Fleischman ........ A61B 17/0401 606/232
2012/0323262 A1* 12/2012 Ibrahim ........... A61B 17/12009 606/144
2013/0345670 A1* 12/2013 Rajagopalan ........ A61B 18/042 606/1
2014/0276810 A1* 9/2014 Raybin ............ A61B 17/32056 606/46
2016/0022273 A1 1/2016 Kassab
2017/0065299 A1* 3/2017 Gillespie ................. A61F 2/962
2020/0100796 A1* 4/2020 Berger ............. A61B 17/12168

OTHER PUBLICATIONS

PCT/US2021/028784, “International Preliminary Report on Patentability,” Nov. 3, 2022, 7 pages.

* cited by examiner 120
110

ENDOCARDIAL LEFT ATRIAL APPENDAGE MANAGEMENT

CROSS-REFERENCE TO RELATED APPLICATIONS

This application is a National Stage application of International Application No. PCT/US2021/028784, filed Apr. 23, 2021, which claims the benefit of and priority to U.S. Provisional Patent Application Ser. No. 63/014,363, filed on Apr. 23, 2020, which are both hereby incorporated by reference as though fully set forth herein.

FIELD

The presently disclosed subject matter relates to methods and devices for managing appendages in a patient subject. In certain embodiments, the methods and devices may be employed for removal of the left atrial appendage of a patient subject.

BACKGROUND

The heart includes four chambers: a right atrium that receives blood from the superior and inferior vena cavas, a right ventricle that pumps blood to the lungs, a left atrium that receives blood from the lungs, and a left ventricle that pumps blood through the aorta to the rest of the body. The left atrial appendage (LAA) is a small, ear-shaped sac in the muscle wall of the left atrium, the top left chamber of the heart. Under normal conditions, the blood in the left atrium and LAA is squeezed out of the left atrium into the left ventricle, the bottom left chamber of the heart, as the heart contracts with each heartbeat.

When a patient has atrial fibrillation (AF), the electrical impulses that control the heartbeat can become fast and chaotic, and the left atrium may not fully contract or effectively squeeze blood into the ventricles. Because the LAA is a small sac, blood can collect within the LAA and clots may form in patients with AF. These blood clots can dislodge from the LAA and may be pumped from the heart, causing the patient to suffer a stroke. AF is a common cardiac arrhythmia that affects more than 33 million individuals, and the incidence is increasing in frequency as the population ages and as screening programs identify asymptomatic AF.

LAA occlusion, also referred to as LAA closure, is a treatment strategy to reduce the risk of blood clots from the LAA from entering the bloodstream and causing a stroke in patients with non-valvular AF. Left atrial appendage management (LAAM) is a persistent clinical challenge related to AF, as well as various other cardiac arrhythmic conditions, various coagulopathies, and concurrent risks of ischemic stroke. Conventional treatment with oral anticoagulation medication can be beneficial in lowering the risk of stroke in AF patients; however, this therapy can have adverse side effects and complications. AF patients may have a contraindication to anticoagulation therapy, which leaves these individuals unprotected.

Surgical suturing of the appendage, surgical application of pericardial appendage clips, and endocardial LAA occlusion are strategies that have been used for stroke prevention in LAAM in patients with an elevated stroke risk. These strategies can be expensive and may present additional risk to the patient, especially for open-heart surgery or pericardial surgical procedures. Conventional endocardial procedures for LAAM may utilize appendage occlusive devices that can leak into the LAA. In some cases, occlusive materials within the LAA can become dislodged from the LAA and pass into the left atrium through the mitral valve into the left ventricle and obstruct the aortic valve or the aorta. Foreign objects placed within the LAA by a transseptal catheter can provide significant long-term risks for these complications.

SUMMARY

Described herein are methods and devices for endocardial left atrial appendage management (LAAM) that engage and invert the left atrial appendage (LAA).

In some embodiments, a method for endocardial left atrial appendage management (LAAM) may comprise inserting an inverter apparatus into an interior cavity of the left atrial appendage (LAA) of a subject, inverting the LAA, positioning one or more closure devices around a base portion of the inverted LAA, closing the base portion of the inverted LAA with the one or more closure devices, positioning a separation apparatus at the base portion of the inverted LAA adjacent to the one or more closure devices, separating the inverted LAA from the left atrium with a separation apparatus, and removing the separated LAA from the subject. The method may include engaging the inverter apparatus with an interior wall of the LAA and pulling the inverter apparatus into the left atrium to invert the LAA. In certain embodiments, the base of the inverted LAA may be substantially aligned with an outer wall of the left atrium. Optionally, the method can further comprise reducing the size of the inverted LAA to facilitate removal of the inverted LAA from the subject. In some embodiments, a size reduction apparatus may be positioned around the inverted LAA in the left atrium and engaged to reduce the size of the inverted LAA.

Also disclosed is a medical device for endocardial LAAM. In some embodiments, a medical device may comprise a head that comprises at least one arm that extends outwardly from a first position of the head, and a handle connected to a second position of the head, where the first position and the second position are opposite one another. In some embodiments, the at least one arm may comprise a hooked, pointed, jagged, or rounded tip. In certain embodiments, the inverter device may include a plurality of arms. In other embodiments, the medical device may comprise a port with negative pressure.

Also disclosed is a kit for endocardial LAAM. In some embodiments, the kit may comprise an inverter apparatus, one or more closure devices; and a separation apparatus. In certain embodiments, the kit may further comprise a size reduction apparatus. Optionally, the kit may include a catheter.

BRIEF DESCRIPTION OF THE DRAWINGS

FIG. 11 is a schematic showing a perspective view of a closure device according to one embodiment described herein.

DETAILED DESCRIPTION

Figure 1:
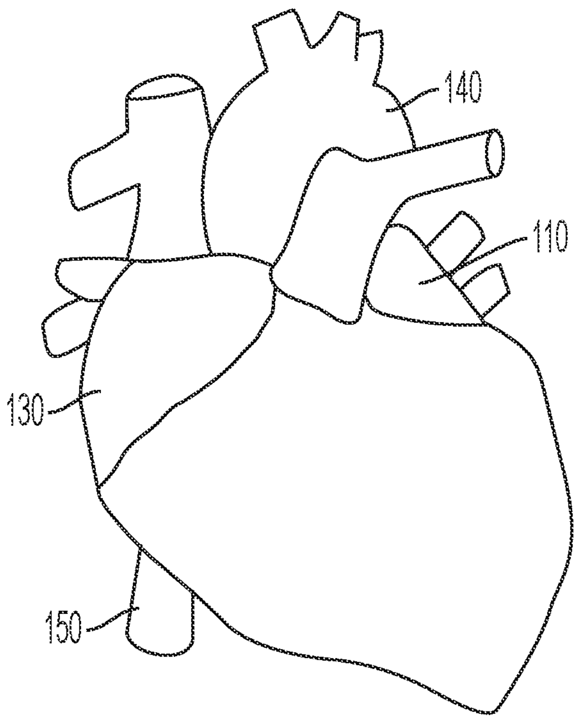
FIG. 1 is a schematic showing a side view of the heart.

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein.

Described herein are methods for endocardial left atrial appendage management (LAAM) that invert the left atrial appendage (LAA). The methods may use a percutaneous trans-septal catheter to engage and invert the LAA, and secure the LAA for excision. The methods for endocardial left atrial appendage management by inversion and excision (ELAAMIE) do not require open-heart surgery or pericardial surgical procedures to clamp or suture the LAA closed. Rather, the methods may use minimally invasive percutaneous access and endocardial procedures used by cardiologists in heart catheterization and endocardial ablation. Endocardial access may be gained via the femoral vein and a trans-septal catheter crossing into the left atrium via the fossa ovale or the atrial septal wall. This approach can allow for lower costs than surgical procedures, increase patient access to the procedure and result in less invasive methods that may bring fewer adverse risks than open heart or pericardial surgical procedures.

The present disclosure may be embodied in a variety of ways. In one embodiment, methods of the present disclosure may comprise inserting an inverter apparatus into an interior cavity of the LAA of a subject, engaging the inverter apparatus with an interior wall of the LAA, inverting the LAA by pulling the inverter apparatus into the left atrium until the LAA is substantially inverted. In some cases, the base of the inverted LAA may be substantially aligned with an outer wall of the left atrium when the LAA inversion is completed. Once the LAA is substantially inverted, the methods further comprise positioning one or more closure devices around a base portion of the inverted LAA and closing the base portion of the inverted LAA with the one or more closure devices to prepare the LAA for excision. To excise the LAA, the methods further comprise positioning a separation apparatus at the base portion of the inverted LAA adjacent to the one or more closure devices, separating the inverted LAA from the left atrium with the separation apparatus, and removing the separated LAA from the subject.

Unlike the other LAAM methods, the ELAAMIE methods may grasp, seize or hold and invert the LAA inside the left atrium, remove the LAA within the atrium, and leave no medical device behind. ELAAMIE can remove the majority of the appendage from the heart and substantially prevent the collection of blood and formation of clots in patients with AF. The amputated closed stump of the LAA may be rapidly repaved by the host endocardium as a natural smooth surface. The percutaneous removal of the LAA through ELAAMIE can provide a long-term solution for managing stroke risk in AF patients. In some cases, patients may be treated for cardiac arrhythmia in a clinical electrophysiology (EP) lab by therapeutic endocardial ablation and may concurrently undergo an ELAAMIE procedure by utilizing the same percutaneous and trans-septal access points.

In some embodiments, the inverter apparatus may be a grasping tool that comprises one or more arms. In some cases, the one or more arms may be articulating. Optionally, the arms of the inverter apparatus may comprise a curved tip, a round or jagged tip, hooks, adherent surfaces with small negative pressure attachments and/or teeth. The tip and/or walls of the inverter apparatus may engage and hold the interior wall of the LAA for inversion while avoiding large penetrations, piercings, or lacerations of the wall of the LAA. The inverter may include a plurality of arms in certain examples. In other examples, the inverter apparatus may engage with the interior wall of the LAA using negative pressure.

Once the LAA is inverted, the base of the appendage may be sealed or closed. In some embodiments, one or more closure devices may be used to prepare the inverted LAA for excision and to ensure the stump of the excised LAA remains closed. For example, one device may be used, two devices may be used, or three or more devices may be used to close the base of the inverted LAA. In some embodiments, the closure device may comprise at least one of a slip knot, a polymeric zipper tie, a clip, an absorbable elastic band, a suture purse string, a barbed suture, a staple, a strip, or combination thereof. In some examples, the multiple closure devices used may differ or may be identical in kind. In some embodiments, a surgical stapler may be used to place the closure device. In certain embodiments, the surgical stapler may utilize bovine or porcine tissue as a closure device. The closure devices can permit the atrium to contract normally, and move blood within the heart once the inverted LAA is excised. In some examples, the closure devices may breakdown and be absorbed by the body. In other examples, the one or more closure devices may remain at the base of the amputated LAA and be quickly covered by proliferation of the host endocardium.

Once the base of the LAA is closed, the inverted LAA may be separated (e.g., cut off). In some cases, the inverter apparatus may remain engaged with the inverted LAA during the separation step. A variety of methods may be used to separate the inverted LAA from the left atrium. In some embodiments, the separation apparatus may comprise a metal wire. For example, the separation apparatus may be a metal noose that may lassoed around the base of the inverted LAA and tightened to separate the LAA. In some embodiments, the separation apparatus may be a guillotine-style cutting apparatus. In other embodiments, the separation apparatus may use electromagnetic radiation to separate the inverted LAA. For example, the electromagnetic radiation may be at frequencies between 350-500 kHz. In other examples, the separation apparatus may use electromagnetic radiation at wavelengths between 800-1500 nm. In some embodiments, the separation apparatus may cauterize the inverted LAA. In certain embodiments, ultrasonic vibration or electric current may be used to cut and cauterize the inverted LAA. The separated LAA may remain engaged with the inverter apparatus. In some cases, the separated LAA may be held or contained by the inverter apparatus.

Once separated, the LAA may be removed from subject. In some examples, the LAA may be removed using the inverter apparatus along the pathway of the catheter. By excising the LAA the ELAAMIE method may eliminate a potential source of arrhythmic electrical pacing that can arise from the LAA. Conventional pericardial mechanical clips or endocardial occlusive devices may not electrically ablate potential aberrant appendage pathways that can contribute to arrhythmias.

Optionally, the method may further comprise positioning a size reduction apparatus around the inverted LAA in the left atrium prior to removing the inverted LAA from the subject. The size reduction apparatus may be engaged to reduce the size of the LAA to facilitate removal of the inverted left appendage from the subject. In some cases, a cross-section of the inverted LAA may be reduced to a width less than a width of a port in the septum. In certain embodiments, a cross-section of the inverted LAA may be reduced to a width of 24 French or less. The size of the separated LAA may be reduced by cutting, crushing, chemical degradation, or other means known by those skilled in the art. In some examples, the size reduction apparatus may comprise articulating arms. Optionally, the size reduction apparatus may further comprise a metallic or polymeric mesh. For example, the arms and/or mesh of the size reduction apparatus may comprise stainless steel, a cobalt chrome alloy, a nickel aluminum alloy, or a nickel titanium alloy, such as Nitinol (available from Memry Corporation, Bethel, CT), or other metal alloy known to those skilled in the art. Optionally, the apparatus may be comprised of a metal alloy coated with a polymer. In certain embodiments, the polymer may be a Polytetrafluoroethylene (PTFE) or GORE-TEX (available from W. L. Gore, Flagstaff, AZ). In some embodiments, the size reduction apparatus may comprise a cutting device. In other embodiments, the size reduction apparatus may comprise degradation chemicals, such as an acid or a base.

In some embodiments, the method may further comprise perforating the left atrium through the septum. In some embodiments, the LAA may be incrementally reduced in size for removal. Portions of the LAA may be separated and removed from the heart. In some cases, portions of the LAA may be separated, reduced in size using a size reduction apparatus, and then removed from the heart.

Illustrative examples are given to introduce the reader to the general subject matter discussed herein and are not intended to limit the scope of the disclosed concepts.

Figure 2:
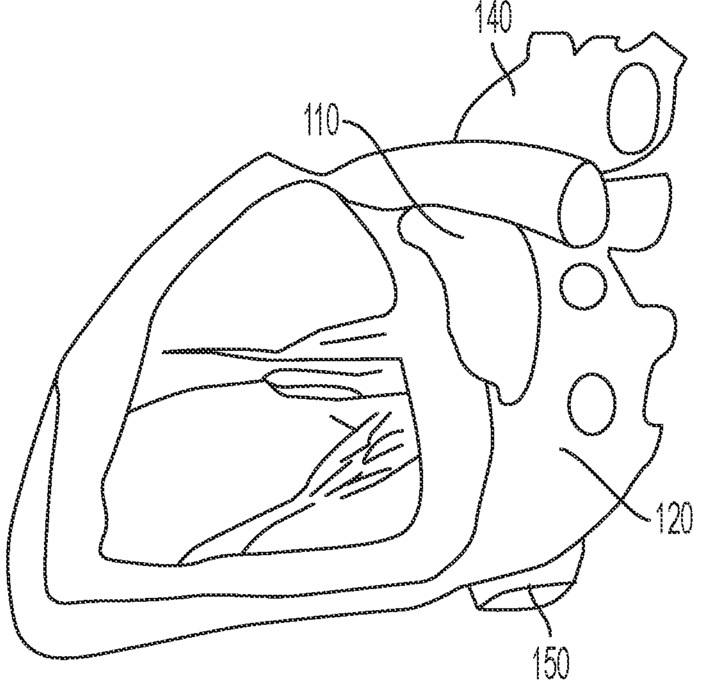
FIG. 2 is a schematic showing a perspective view of the exterior of the left atrium of the heart.
Figure 3:
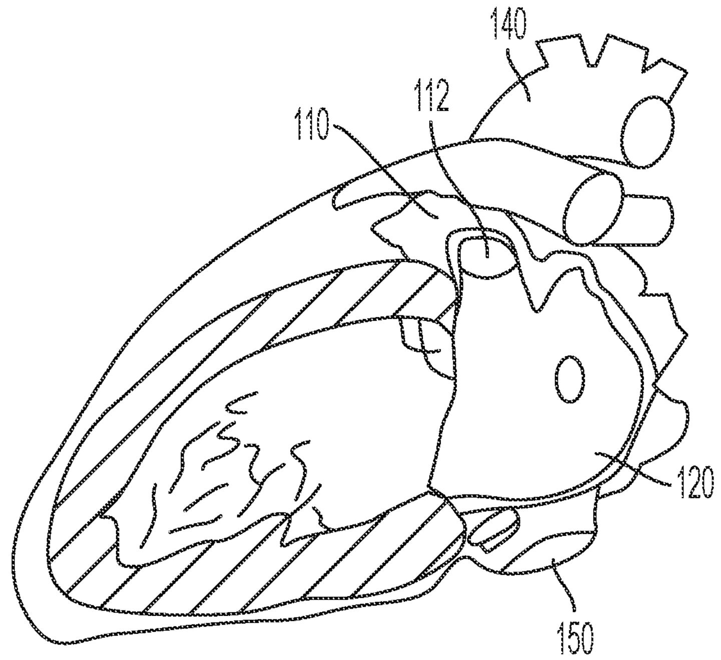
FIG. 3 is a schematic showing a perspective view of the interior of the left atrium of the heart.

FIG. 1 depicts the exterior of the heart, with the LAA 110 opposite of the right atrium 130, the inferior vena cava 150 connected to the right atrium 130, and the aorta 140 extending from the left ventricle. FIG. 2 shows an exterior view of the left atrium 120 with the LAA 110. FIG. 3 depicts an interior view of the left atrium 120, where the cavity 112 of the LAA 110 is visible.

Figures 4A, 4B:
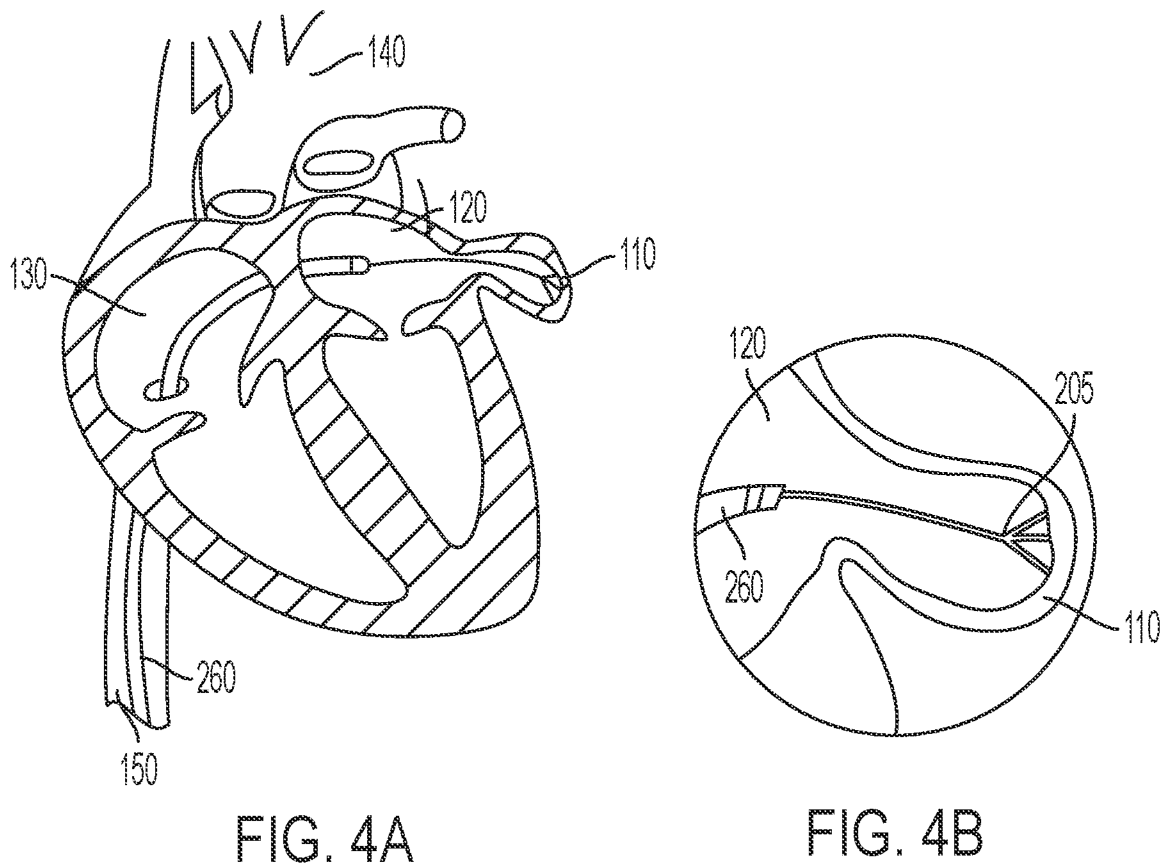
FIGS. 4A to 4E are schematics showing a side view of the LAA before, during, and after inversion, according to one embodiment described herein.

FIG. 4A depicts the positioning of the internal guide wire 260 within the heart. The guidewire 260 can be placed within the inferior vena cava 150 to access the interior of the heart through the right atrium 130 to reach the left atrium 120 and LAA 110. Medical devices, such as an inverter apparatus, can be placed using the guidewire 260 to access the left atrium 120 and LAA 110. FIG. 4B shows the inverter apparatus 205 extending from the guide wire 260 into the LAA 100, where the inverter apparatus 205 grasps the wall of the LAA 110.

Once the inverter apparatus grasps the wall of the LAA, the inverter apparatus can be partially retracted from the LAA while remaining engaged with the wall of the LAA, to invert the LAA within the left atrium.

Figure 4C:
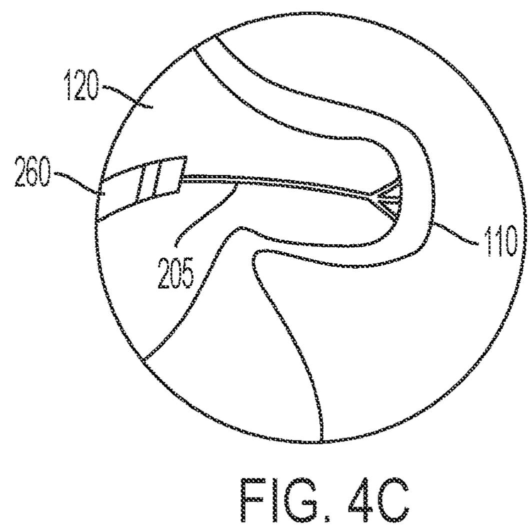
Figure 4D:
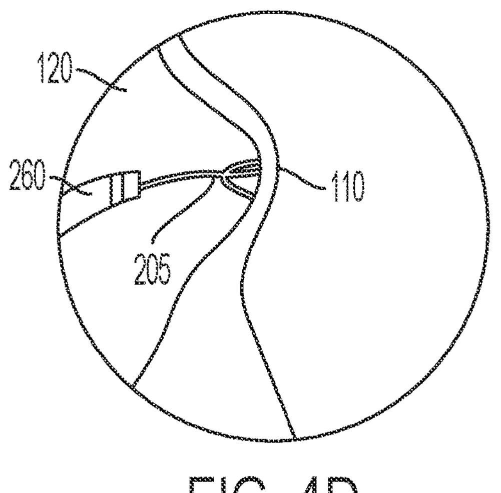
Figure 4D:
Figure 4E:
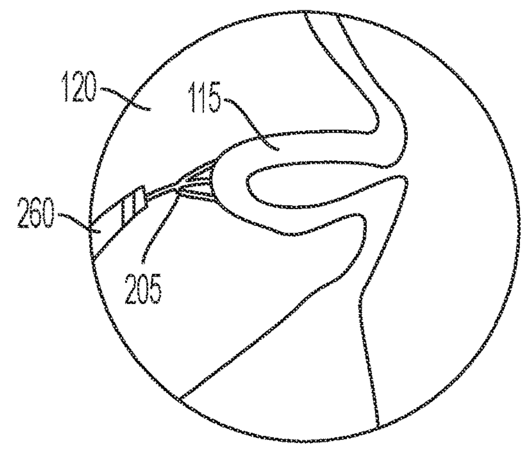

FIGS. 4B to 4E show the stages of LAA inversion. In FIG. 4B, the inverter apparatus 205 is engaged with the wall of the LAA 110. As shown in FIGS. 4C and 4D, as the inverter apparatus 205 is pulled toward the guide wire and into catheter 260, and the LAA 110 can deform to invert (i.e., turn inside-out). The LAA 110 can continue to deform and invert as the inverter apparatus 205 is pulled in a direction away from the LAA 110. As shown in FIG. 4E, the LAA can be fully inverted 115 inside the left atrium 120. The inverter apparatus 205 remains attached to the portion of the LAA 110 that was the interior wall and becomes the tip of the inverted LAA 115.

Figure 5:
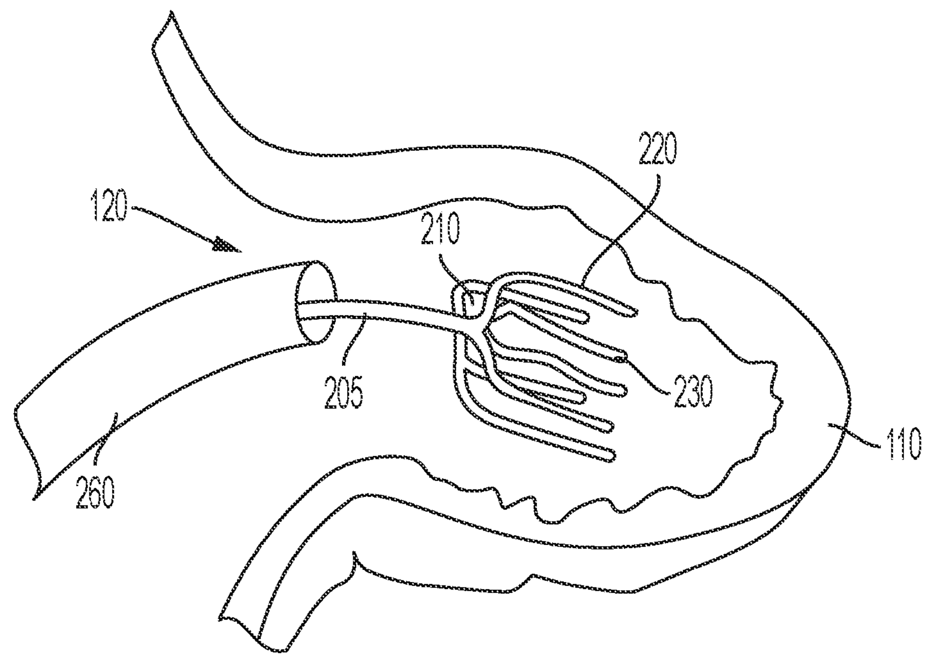
FIG. 5 is a schematic showing a perspective view of an inverter apparatus in the LAA according to one embodiment described herein.
Figure 6:
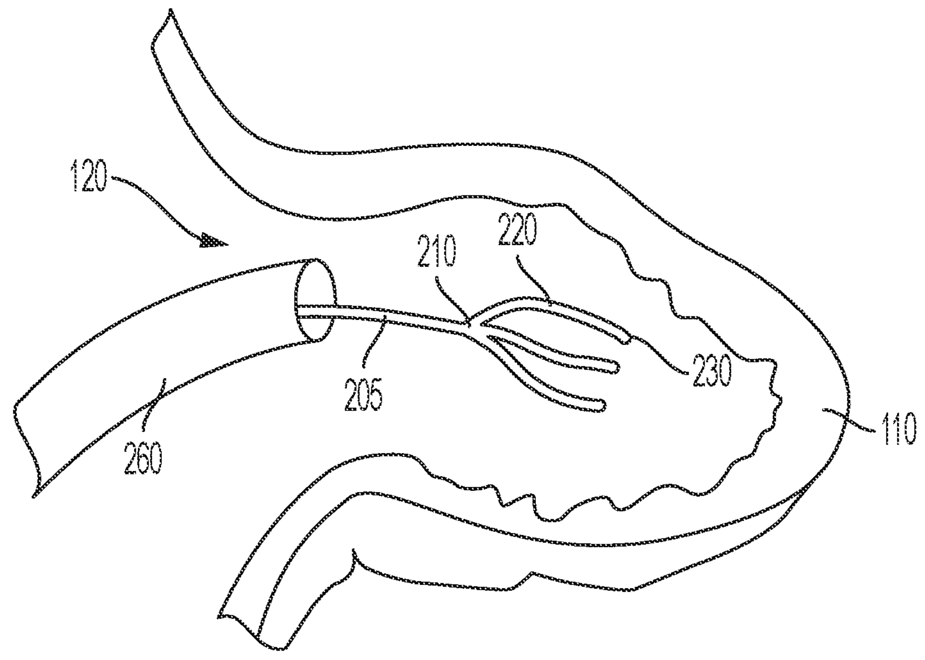
FIG. 6 is a schematic showing a perspective view of an inverter apparatus in the LAA according to one embodiment described herein.
Figure 7:
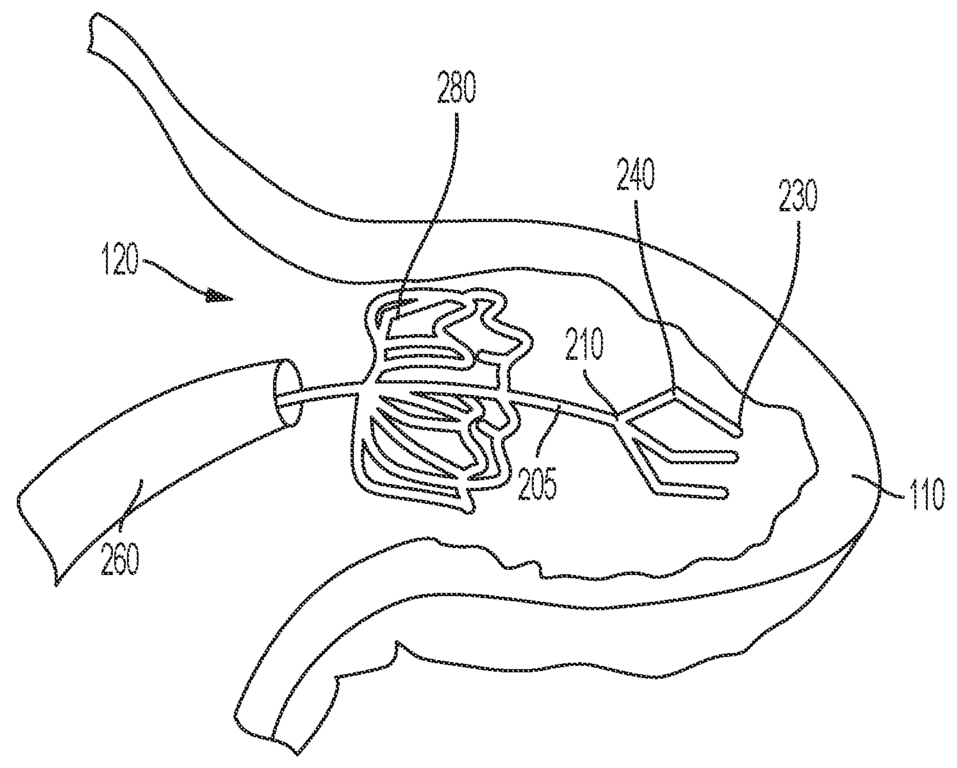
FIG. 7 is a schematic showing a perspective view of an inverter apparatus with size reduction apparatus in the LAA according to one embodiment described herein.

FIGS. 5 to 7 depict various embodiments of the inverter apparatus 205 extending from the internal guidewire 260 through the left atrium 120 into the LAA 110. As shown in FIG. 5, the inverter apparatus 205 may comprise a collapsible head 210 the includes multiple arms 220. The arms 220 can include a blunted tip or rounded end feature 230. The head 210 can be in a collapsed state during transport through the internal guidewire 260. Upon exiting the catheter and internal guidewire 260, the head 210 may be transitioned from a collapsed state to an open state. In the open state, the head 210 can include a plurality of arms 220 that reach the end of the LAA 110, to the wall of the LAA 110 with the tips 230, and grasp the surface of the LAA 110 with sufficient strength to retain a grasp on the LAA 110 as the inverter apparatus 205 is pulled into the internal guidewire 260 to invert the LAA into the left atrium 120. In some cases, the head 210 may be simplified to include only two or three arms 220, as depicted in FIG. 6. In some embodiments, the arms of the inverter apparatus 205 may be articulated. As shown in FIG. 7, the inverter apparatus 205 can include articulated arms 240 that can extend from and contract toward the center of the inverter apparatus 205. The articulation of the arms may aid in obtaining a strong grasp on the LAA 110 for inversion. A size reduction apparatus 280 can be used to reduce the physical size of the LAA for extraction. As shown in the example illustrated in FIG. 7, the size reduction apparatus 280 can be integrated with the inverter apparatus 205. The size reduction apparatus 280 may include a mesh material that can receive the LAA 110 or a portion of the LAA 110 upon inversion and excision. The size reduction apparatus 280 may be collapsible for transport through the catheter and internal guidewire 260. Upon exiting the catheter and internal guidewire 260, the size reduction apparatus 280 may transition from a collapsed state to an open state ready to receive at least a portion of the inverted LAA.

Figure 8:
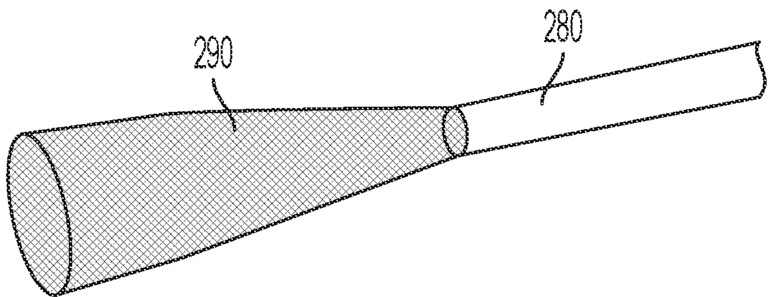
FIG. 8 is a schematic showing a perspective view of a size reduction apparatus according to one embodiment described herein.

As shown in FIG. 8, one embodiment of the size reduction apparatus 280 may have an elongated or conical opening

290 that can receive at least a portion of the inverted LAA and compress the portion of the LAA to aid in removal of the portion of LAA from the left atrium via the internal guide wire through the catheter.

Figures 9A, 9B, 9C, 9D, 9E, 9F, 9G, 9H, 9I, 9J:
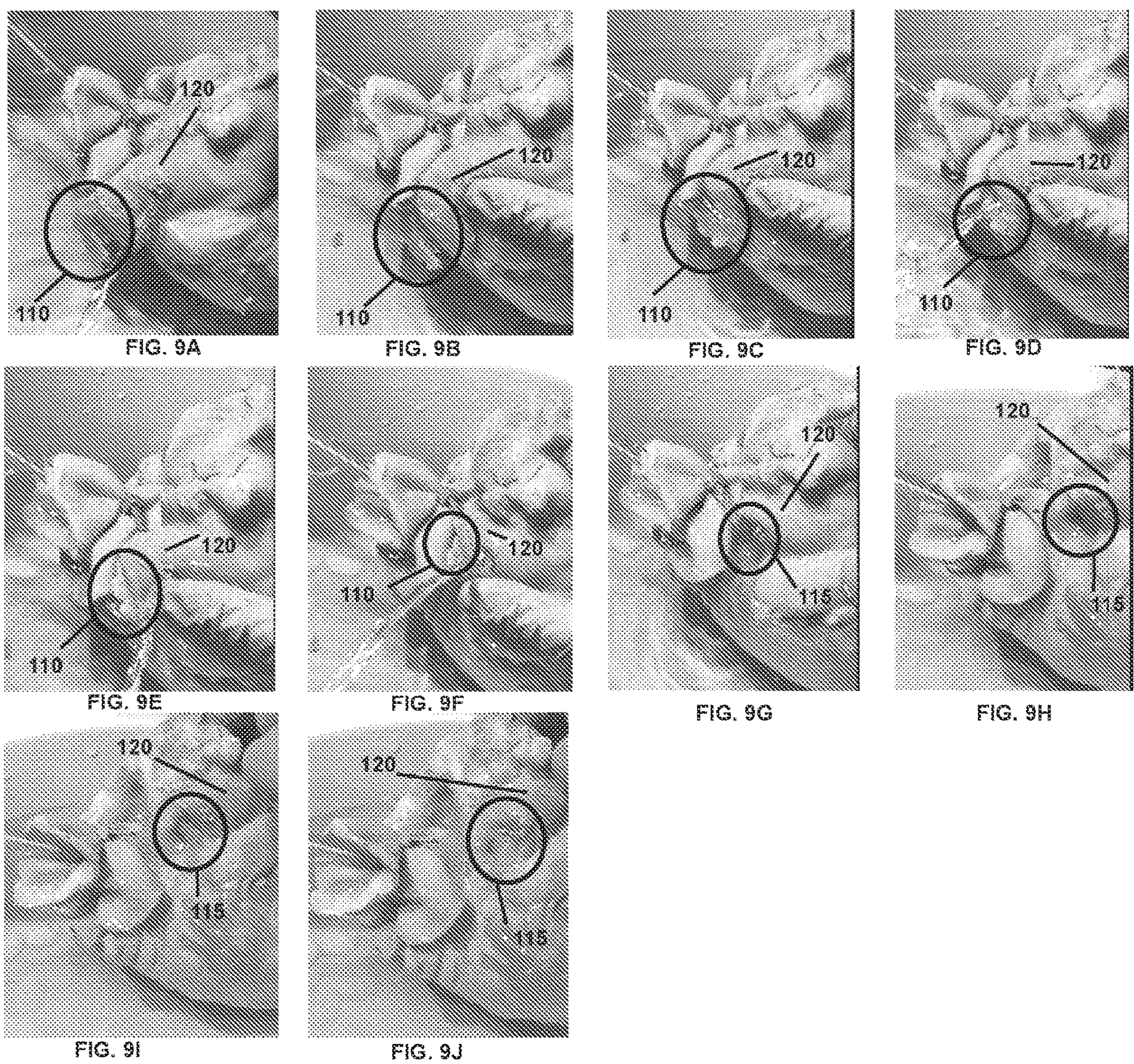
FIGS. 9A to 9J are photographs of the exterior of the heart, with the LAA being inverted according to one embodiment described herein.

FIGS. 9A to 9J show an exterior view of successive stages of an inversion of the LAA 110 into the left atrium 120. As shown in FIGS. 9A and 9B, the LAA 110 extends from the left atrium 120 of the heart. When the inverter apparatus (not shown) engages with the interior wall of the LAA, and is retracted into the catheter, the LAA can be pulled into the left atrium and inverted (see FIGS. 4A to 4D). As shown in FIGS. 9C to 9F, the LAA 110 can be pulled within the left atrium 120 and then inverted. Once within the left atrium 120, the inverted LAA 115 may become part of the exterior wall of the heart, as shown in FIGS. 9G to 9J.

Figure 10A:
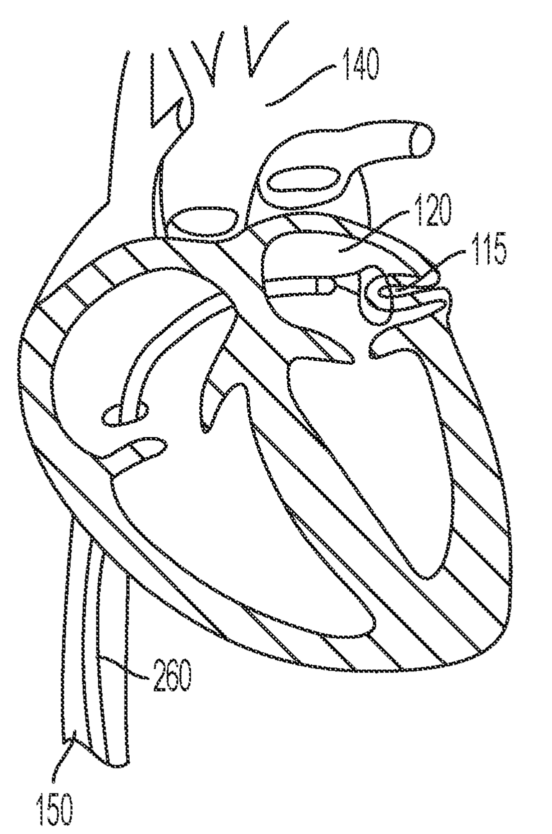
FIGS. 10A to 10C are schematics showing a side view of an inverted LAA during and after closure according to one embodiment described herein.
Figure 10A:
Figure 10B:
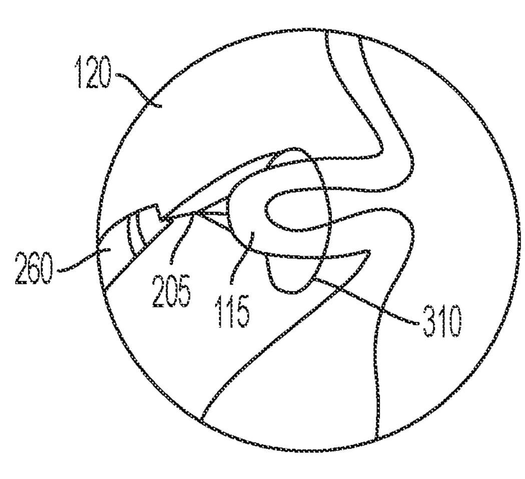
Figure 10C:
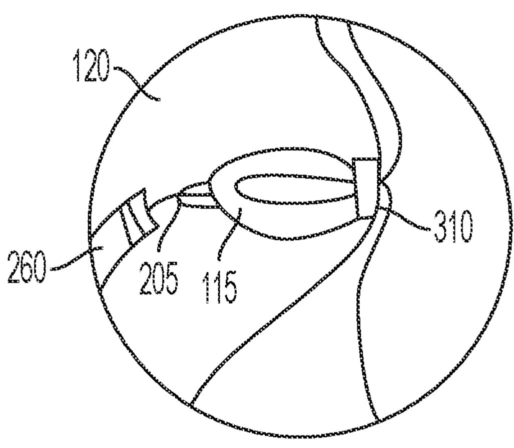
Figure 11:
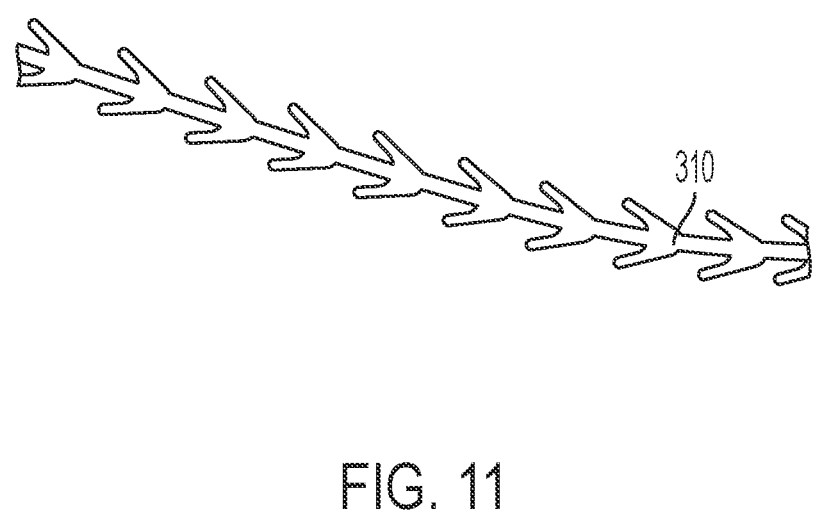

As shown in FIGS. 10A to 10C, once pulled into the left atrium 120, the inverted LAA 115 can be closed using one or more closure devices 310. The closure device 310 can be a self-closing tie, a suture, a band, or other closure device. The closure device 310 can slip over the inverted LAA 115, with the inverter apparatus 205 remaining engaged. A barbed suture, shown in FIG. 11, is one example of a closure device 310 that can be used.

Figures 12A, 12B, 12C:
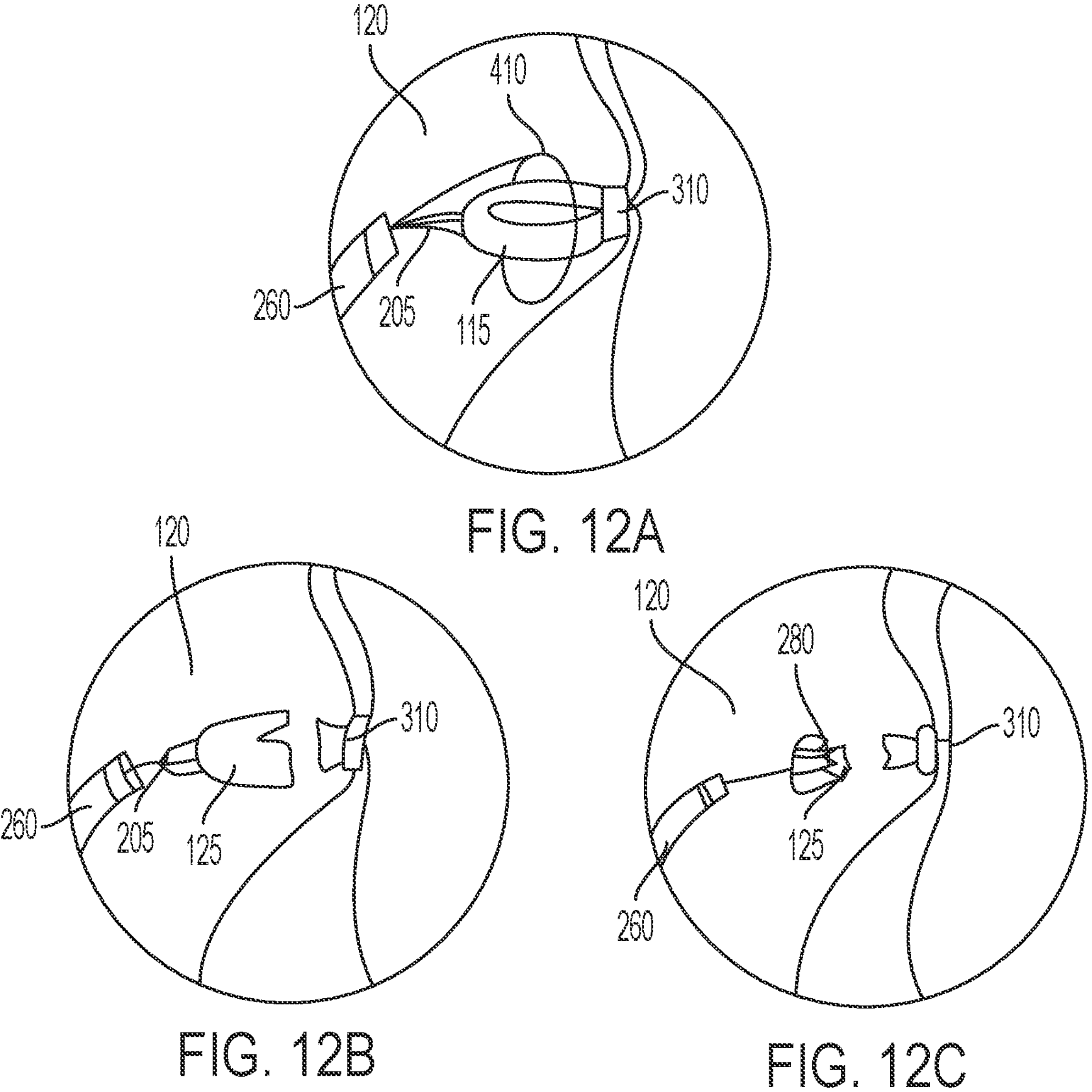
FIGS. 12A to 12C are schematics showing a side view of an inverted LAA during and after separation according to one embodiment described herein.

Once the inverted LAA 115 is closed using closure device 310, the tissue of the inverted LAA 115 can be separated, as shown in FIGS. 12A to 12C. The closure device 310 can remain in place during and after the separation of at least a portion of the inverted LAA 115. As shown in FIG. 12A, the separation apparatus 410 can slip over or around the inverted LAA 115, with the inverter apparatus 205 remaining engaged. In some embodiments, once the inverted LAA is separated, the separated LAA 125 may be removed from the heart using the inverter apparatus 205, as shown in FIG. 12B. In some embodiments, the separated LAA 125 may be too large to remove through the catheter along the guide wire 260. A size reduction apparatus 280 can be used to reduce the size of the excised LAA for removal, as shown in FIG. 12C.

Figure 13:
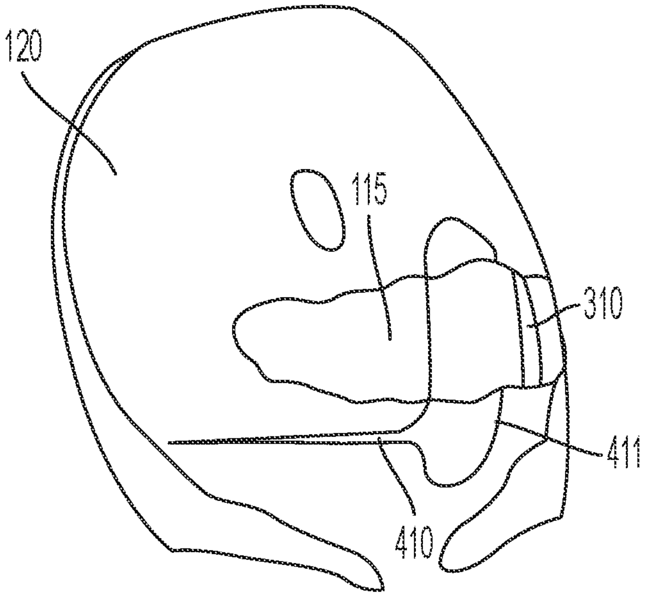
FIG. 13 is a schematic showing a perspective view of a separation apparatus according to one embodiment described herein.
Figure 14:
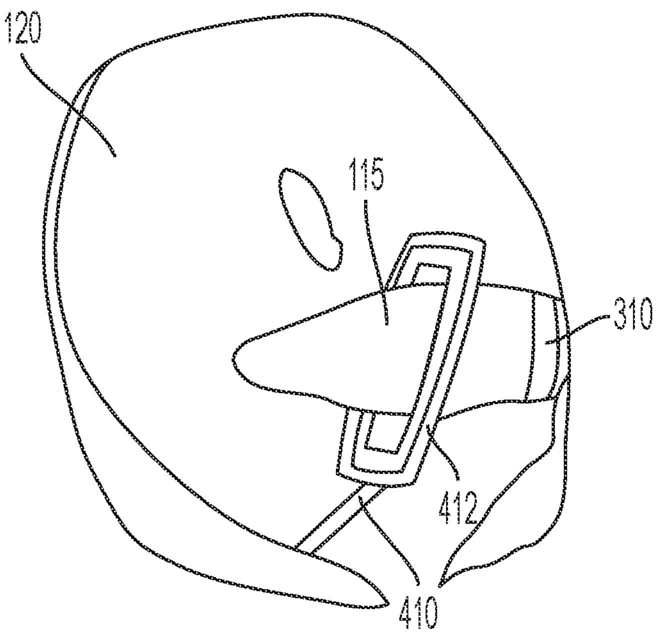
FIG. 14 is a schematic showing a perspective view of a separation apparatus according to one embodiment described herein.
Figure 15:
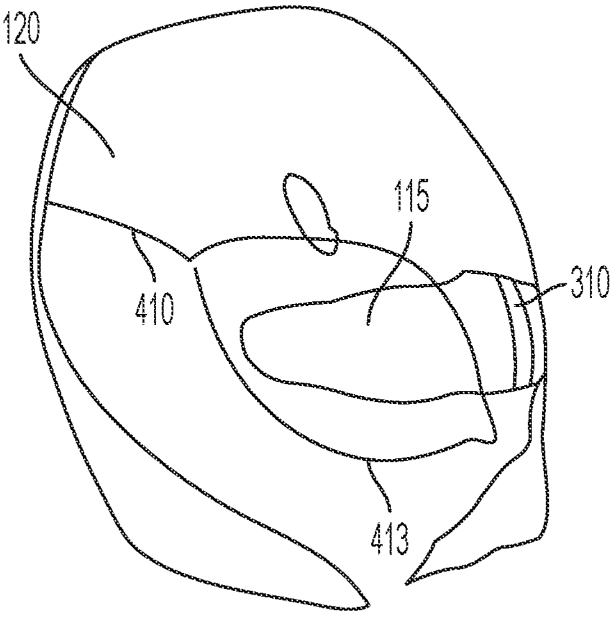
FIG. 15 is a schematic showing a perspective view of a separation apparatus according to one embodiment described herein.

FIGS. 13 to 15 depict various embodiments of the separation apparatus 410 extending into the left atrium 120 to separate the inverted LAA 115. As shown in FIG. 13, the separation apparatus 410 may comprise a cutting wire 411. The cutting wire 411 may be placed around the inverted LAA 115 and moved substantially perpendicular to the inverted LAA 115 to cut the inverted LAA 115 and cleave it from the left atrium 120. In some cases, the separation apparatus 410 may comprise a guillotine-style cutter 412, as shown in FIG. 14. The cutter 412 may be placed around the inverted LAA 115 and engaged to slice the inverted LAA 115 from the left atrium 120. As shown in FIG. 15, the separation apparatus 410 may comprise a cutting device 413. The cutting device 413 may be placed around the inverted LAA 115 and moved substantially perpendicular to the inverted LAA 115 to cut the inverted LAA 115 and cleave it from the left atrium 120. In other embodiments, a cutting device may be used to slice the inverted LAA from the side and may not surround the inverted LAA.

In certain embodiments, the inverter apparatus and size reduction apparatus may be integrated in a single apparatus. In other embodiments, the inverter apparatus, size reduction apparatus, and separation apparatus may be integrated into a single apparatus.

In other embodiments, the present disclosure comprises a medical device. The medical device may comprise a head comprising at least one arm extending outwardly from a first position of the head and a handle connected to a second position of the head. In some embodiments, the first position is approximately 180 degrees from the second position. In some embodiments, the at least one arm may comprise a hooked, pointed, jagged, or rounded tip. The head may comprise a plurality of arms in some examples. In some examples, the medical device may further comprise a mesh.

The at least one arm of the medical device may articulate and/or rotate about the head of the device. In certain examples, the device may comprise a plurality of arms that move in a lateral direction at the head. For example, the device may comprise two arms that rotate towards one another and act as a set of pinchers.

The medical device may comprise a metal alloy or polymeric coating. For example, the arms and/or mesh of the size reduction apparatus may stainless steel, a cobalt chrome alloy, a nickel aluminum alloy, or a nickel titanium alloy, such as Nitinol (available from Memry Corporation, Bethel, CT), or other metal alloy known to those skilled in the art. Optionally, the apparatus may be comprised of a metal alloy coated with a polymer. In certain embodiments, the polymer may be a Polytetrafluoroethylene (PTFE) or GORE-TEX (available from W. L. Gore, Flagstaff, AZ).

In some embodiments, the handle may further comprise a lever to articulate the at least one arm. In some cases, the medical device may be an inverter device.

In other embodiments, the present disclosure comprises a kit for ELAAMIE, the kit comprising an inverter apparatus, one or more closure devices, and a separation apparatus, as described herein. Optionally, the kit may further comprise a size reduction apparatus. In certain embodiments, the kit may include a percutaneous trans-septal catheter.

The terms "a", "an", and "the" refer to "one or more" when used in this application, including the claims. Thus, for example, reference to "an arm" includes a plurality of such arms, unless the context clearly is to the contrary (e.g., a plurality of arms), and so forth.

Various embodiments of the disclosure have been described herein. It should be recognized that these embodiments are merely illustrative of the present disclosure. Variations of those preferred embodiments may become apparent to those of ordinary skill in the art upon reading the foregoing description. It is expected that skilled artisans can employ such variations as appropriate, and the disclosure is intended to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated or otherwise clearly contradicted by context.

Illustrative Embodiments of Suitable Methods and Devices

As used below, any reference to methods, devices, or kits is understood as a reference to each of those methods, devices, or kits disjunctively (e.g., "Illustrative embodiment 1-4 is understood as illustrative embodiment 1, 2, 3, or 4.").

Illustrative embodiment 1 is a method for left atrial appendage management comprising: inserting an inverter apparatus into an interior cavity of the left atrial appendage of a subject; engaging the inverter apparatus with an interior wall of the left atrial appendage; inverting the left atrial appendage by pulling the inverter apparatus into the left atrium until the left atrial appendage is substantially inverted; positioning one or more closure devices around a base portion of the inverted left atrial appendage; closing the base portion of the inverted left atrial appendage with the one or more closure devices; positioning a separation apparatus at the base portion of the inverted left atrial appendage adjacent to the one or more closure devices; separating the inverted left atrial appendage from the left atrium with the separation apparatus; and removing the separated left atrial appendage from the subject.

Illustrative embodiment 2 is the method of any preceding or subsequent illustrative embodiment, wherein the inverter apparatus comprises a plurality of arms.

Illustrative embodiment 3 is the method of any preceding or subsequent illustrative embodiment, wherein each of the plurality of arms comprise a curved end.

Illustrative embodiment 4 is the method of any preceding or subsequent illustrative embodiment, wherein the inverter apparatus engages the interior wall using negative pressure.

Illustrative embodiment 5 is the method of any preceding or subsequent illustrative embodiment, wherein the closure device comprises at least one of a slip knot, a band, a polymeric zipper tie, or combination thereof.

Illustrative embodiment 6 is the method of any preceding or subsequent illustrative embodiment, wherein the base of the inverted left atrial appendage is substantially aligned with an outer wall of the left atrium.

Illustrative embodiment 7 is the method of any preceding or subsequent illustrative embodiment, wherein the separation apparatus comprises a metal wire.

Illustrative embodiment 8 is the method of any preceding or subsequent illustrative embodiment, wherein the separation apparatus uses electromagnetic radiation at frequencies between 350-500 kHz.

Illustrative embodiment 9 is the method of any preceding or subsequent illustrative embodiment, wherein the separation apparatus uses electromagnetic radiation at wavelengths between 800-1500 nm.

Illustrative embodiment 10 is the method of any preceding or subsequent illustrative embodiment, wherein the separated left atrial appendage remains engaged by the inverter apparatus.

Illustrative embodiment 11 is the method of any preceding or subsequent illustrative embodiment, further comprising perforating the left atrium through the septum.

Illustrative embodiment 12 is the method of any preceding or subsequent illustrative embodiment, further comprising: prior to removing the inverted left atrial appendage from the subject, positioning a size reduction apparatus around the inverted left atrial appendage in the left atrium; and engaging the size reduction apparatus to reduce the size of the left atrial appendage to facilitate removal of the inverted left appendage from the subject.

Illustrative embodiment 13 is the method of any preceding or subsequent illustrative embodiment, wherein a cross-section of the inverted left atrial appendage is reduced to a width of 24 French or less.

Illustrative embodiment 14 is the method of any preceding or subsequent illustrative embodiment, wherein a cross-section of the inverted left atrial appendage is reduced to a width less than a width of a port in the septum.

Illustrative embodiment 15 is the method of any preceding or subsequent illustrative embodiment, wherein the size reduction apparatus comprises articulating arms.

Illustrative embodiment 16 is the method of any preceding or subsequent illustrative embodiment, wherein the size reduction apparatus further comprises a metallic or polymeric mesh.

Illustrative embodiment 17 is the method of any preceding or subsequent illustrative embodiment, wherein the mesh comprises stainless steel, a cobalt chrome alloy, a nickel aluminum alloy, or a nickel titanium alloy.

Illustrative embodiment 18 is the method of any preceding or subsequent illustrative embodiment, wherein the size reduction apparatus comprises a cutting device.

Illustrative embodiment 19 is the method of any preceding illustrative embodiment, wherein the size reduction apparatus comprises an acid or base.

Illustrative embodiment 20 is a medical device comprising: a head comprising at least one arm extending outwardly from a first position of the head, wherein the at least one arm comprises at least one of a hooked, pointed, jagged, or rounded tip; and a handle connected to a second position of the head.

Illustrative embodiment 21 is the medical device of any preceding or subsequent illustrative embodiment, wherein the head comprises a plurality of arms.

Illustrative embodiment 22 is the medical device of any preceding or subsequent illustrative embodiment, wherein the plurality of arms move in a lateral direction at the head.

Illustrative embodiment 23 is the medical device of any preceding or subsequent illustrative embodiment, wherein the at least one arm is articulating.

Illustrative embodiment 24 is the medical device of any preceding or subsequent illustrative embodiment, wherein the handle further comprises a lever to articulate the at least one arm.

Illustrative embodiment 25 is the medical device of any preceding or subsequent illustrative embodiment, wherein the device comprises stainless steel, a cobalt chrome alloy, a nickel aluminum alloy, or a nickel titanium alloy.

Illustrative embodiment 26 is the medical device of any preceding or subsequent illustrative embodiment, wherein the device comprises a polymeric coating.

Illustrative embodiment 27 is the medical device of any preceding or subsequent illustrative embodiment, further comprising a metallic or polymeric mesh.

Illustrative embodiment 28 is the medical device of any preceding illustrative embodiment, wherein the mesh comprises stainless steel, a cobalt chrome alloy, a nickel aluminum alloy, or a nickel titanium alloy.

Illustrative embodiment 29 is a kit comprising: an inverter apparatus; one or more closure devices; and a separation apparatus.

Illustrative embodiment 30 is the kit of any preceding or subsequent illustrative embodiment, further comprising a size reduction apparatus.

Illustrative embodiment 31 is the kit of any preceding illustrative embodiment, further comprising a catheter.

Illustrative embodiment 32 is a kit comprising the medical device of any preceding illustrative embodiment; one or more closure devices; and a separation apparatus.

What is claimed is:

1. A method for left atrial appendage management comprising:

inserting an inverter apparatus into an interior cavity of the left atrial appendage of a subject;

engaging the inverter apparatus with an interior wall of the left atrial appendage;

inverting the left atrial appendage by pulling the inverter apparatus into the left atrium until the left atrial appendage is substantially inverted;

positioning one or more closure devices around a base portion of the inverted left atrial appendage;

closing the base portion of the inverted left atrial appendage with the one or more closure devices;

positioning a size reduction apparatus having an integrated cutting device around the inverted left atrial appendage in the left atrium;

separating the inverted left atrial appendage from the left atrium at the base portion of the inverted left atrial appendage adjacent to the one or more closure devices with the integrated cutting device; and removing the separated left atrial appendage from the subject.

2. The method of claim 1, wherein the inverter apparatus comprises a plurality of arms.

3. The method of claim 2, wherein each of the plurality of arms comprise a curved end.

4. The method of claim 1, wherein the closure device comprises of a slip knot, a band, a polymeric zipper tie, or combinations thereof.

5. The method of claim 1, wherein the base of the inverted left atrial appendage is substantially aligned with an outer wall of the left atrium.

6. The method of claim 1, wherein the integrated cutting device comprises a metal wire.

7. The method of claim 1, wherein the integrated cutting device uses electromagnetic radiation at frequencies between 350-500 kHz.

8. The method of claim 1, wherein the integrated cutting device uses electromagnetic radiation at wavelengths between 800-1500 nm.

9. The method of claim 1, wherein the separated left atrial appendage remains engaged by the inverter apparatus.

10. The method of claim 1, further comprising:

prior to removing the inverted left atrial appendage from the subject, engaging the size reduction apparatus to reduce the size of the left atrial appendage to facilitate removal of the inverted left appendage from the subject.

11. The method of claim 10, wherein a cross-section of the inverted left atrial appendage is reduced to a width of 24 French or less.

12. The method of claim 10, wherein the size reduction apparatus comprises articulating arms.

13. The method of claim 12, wherein the size reduction apparatus further comprises a metallic or polymeric mesh.

14. The method of claim 10, wherein size reduction is achieved by cutting, crushing, compression, or chemical degradation.

15. The method of claim 1, wherein the integrated cutting device comprises ultrasonic vibration.

* * * * *